United States Patent [19]

Scharf et al.

[11] 4,250,119

[45] Feb. 10, 1981

[54] PROCESS FOR THE PRODUCTION OF ACETONE FROM ISOBUTYRALDEHYDE

[75] Inventors: Helmut Scharf, Schermbeck; Gerhard Franz; Günther Hökele, both of Marl, all of Fed. Rep. of Germany

[73] Assignee: Chemische Werke Huls Aktiengesellschaft, Marl, Fed. Rep. of Germany

[21] Appl. No.: 931,665

[22] Filed: Aug. 7, 1978

[30] Foreign Application Priority Data

Aug. 25, 1977 [DE] Fed. Rep. of Germany ....... 2739269

[51] Int. Cl.³ ............................................. C07C 45/32
[52] U.S. Cl. .................................... 568/389; 252/442
[58] Field of Search .................... 260/593 R; 252/442

[56] References Cited

U.S. PATENT DOCUMENTS

| 3,344,085 | 9/1967 | Isacks et al. | 252/447 |
| 3,767,711 | 10/1973 | Gobron et al. | 260/593 R |
| 3,855,304 | 12/1974 | Sakakibara et al. | 260/593 R |
| 3,987,103 | 10/1976 | Gobron et al. | 260/593 R |
| 4,000,199 | 12/1976 | Obenaus et al. | 260/593 R |

OTHER PUBLICATIONS

Droste et al., Chem. Abst. vol. 83, p. 435, #58026t (1975).

Primary Examiner—James H. Reamer
Attorney, Agent, or Firm—Gilbert L. Wells

[57] ABSTRACT

Isobutyraldehyde is produced by the oxo process and converted to acetone in the gas phase by oxidative decarbonylation on a zinc oxide supported copper oxide catalyst. The conversion is improved by adding about 2.5 to 25 percent by weight graphite to the catalyst, based on the total weight of catalyst.

13 Claims, No Drawings

PROCESS FOR THE PRODUCTION OF ACETONE FROM ISOBUTYRALDEHYDE

CROSS REFERENCE TO A RELATED APPLICATION

Applicants claim priority under 35 USC 119 for application Pat. No. 27 38 269.0 filed Aug. 25, 1977 in the Patent Office of the Federal Republic of Germany.

BACKGROUND OF THE INVENTION

The field of the invention is Chemistry, carbon compounds of acyclic ketones and the invention is particularly concerned with a process for the selective manufacture of acetone by catalytic oxidative decarbonylation of isobutyraldehyde.

Isobutyraldehyde, which is obtained in very large amounts as an unavoidable by-product in the manufacture of n-butylraldehyde from propylene by the oxo synthesis, has hitherto been used almost exclusively only in power stations, for its calorific value.

The state of the art of isobutyraldehyde manufacture by the oxo process may be ascertained by reference to the "Kirk-Othmer Encyclopedia of Chemical Technology", Second Edition, Volume 14 (1967), pages 373-390, particularly pages 380 and 381 where it is disclosed in FIG. 2 and the text that when propylene is the olefin feed, isobutyraldehyde is a less desirable product. The state of the art of isobutyraldehyde conversion to acetone may be ascertained by reference to U.S. Pat. Nos. 3,804,902; 3,855,304 and 4,000,199; the disclosures of which are incorporated herein.

In the process disclosed in U.S. Pat. Nos. 3,804,902 and 3,855,304 isobutyraldehyde is oxidized to acetone in the gas phase with oxygen, on a catalyst consisting of manganese oxide and optionally an alkali metal oxide on activated aluminum oxide support. However, with an isobutyraldehyde conversion of 98 percent, the yield of acetone is still only 83 mole percent.

A substantially better selectivity is shown by the process disclosed in U.S. Pat. No. 4,000,199 whic has the same assignee as the present invention. In the process of U.S. Pat. No. 4,000,199 isobutyraldehyde is oxidized in the gas phase, on a catalyst consisting of copper II oxide with and without an inert support. The best selectivity which can be achieved, as disclosed in Example 6, is 96 mol percent and this is achieved on a catalyst with zinc oxide as the support. The isobutyraldehyde conversion is still only 90.5%.

U.S. Pat. No. 4,000,199 discloses in Column 3, line 35 the use of graphite as "an auxiliary tabletting agent" or mold lubricant but the concentration of graphite in the total catalyst is usually less than 2.5 weight percent.

Since as complete as possible an isobutyraldehyde conversion is necessary for economical commercial production of acetone, the isobutyraldehyde conversions and acetone yields achieved by the process of U.S. Pat. No. 4,000,199 which are in themselves already very good, are still not satisfactory for commercial production. In addition to the high conversion, a high selectivity, in particular, is also of great importance for the commercial profitability of a process of this type.

It is known that the throughput over the catalyst (that is the amount of isobutyraldehyde fed in per unit time) must be matched with the capability of removing the heat of reaction liberated, in order to avoid too steep a temperature profile with selectivity reducing high peak temperatures. A reduction of the total combustion permits a correspondingly higher throughput over the catalyst and thus a higher space/time yield of acetone. However, the space/time yield, that is to say the amount of product obtainable per catalyst volume and per unit time, is always highly important for a large-scale industrial process. In the case of total combustion of isobutyraldehyde, about five times more heat is liberated than in the case of partial oxidation of isobutyraldehyde to acetone. Even if only 4 mol percent of isobutyraldehyde undergoes total combustion in the process, to give not acetone but carbon dioxide and water, about one-fifth of the heat to be removed during the process can be attributed to this 4 mol percent of isobutyraldehyde which has undergone total combustion. Even small improvements in the activity and the selectivity therefore represent a considerable advance over the prior art.

SUMMARY OF THE INVENTION

An object of the present invention is to improve upon the process disclosed in U.S. Pat. No. 4,000,199, particularly the process disclosed in Example 6 with respect to the catalyst selectivity and activity.

This object is achieved in the present invention by manufacturing acetone by catalytic oxidative decarbonylation of isobutyraldehyde in the gas phase by passing a mixture of isobutyraldehyde and oxygen or other oxygen containing gas at elevated temperatures and with a contact time of about 0.1 to 10 seconds over a zinc oxide supported catalyst containing copper oxide, which contains, in addition to copper oxide, 2.5 to 25 percent by weight of graphite, relative to the freshly prepared catalyst. A gaseous mixture of about 1 to 8 percent by volume of isobutyraldehyde and at least the stoichiometric amount of oxygen and optionally an inert diluent is passed over the catalyst.

The copper in the freshly prepared catalysts employed in the process of the present invention consists essentially of copper II oxide but the oxidation stage of the copper oxide during the catalytic oxidative decarbonylation of the present invention is not known. The copper oxide concentration of the supported catalyst is not critical and about 0.1 to 10 percent by weight of copper II oxide in the freshly prepared catalyst is used.

DESCRIPTION OF THE PREFERRED EMBODIMENTS

It is particularly surprising that the copper oxide/zinc oxide supported catalyst disclosed in Example 6 of U.S. Pat. No. 4,000,199 can be improved by the addition of graphite.

The graphite content in the freshly made catalyst is about 2.5 to 25 percent by weight. Above 25 percent by weight and below 2.5 percent by weight, catalyst particles can be manufactured only with great difficulty using the agents customary in industry.

Graphite contents of 3 to 10 percent by weight are preferred, because higher graphite contents bring no further improvements. Commercially available graphite with a purity of 96% and more may be used as the graphite. Types of graphite with a purity of more than 98% are preferred. In order to ensure good distribution of the graphite, the graphite should be in as finely divided a form as possible. So-called colloidal graphite, in which, for example, 95% of the graphite particles have a particle size of 0 to 4 $\mu$m, has proved particularly suitable.

Commercially available grades of zinc oxide may be employed for the zinc oxide used as the support. In general, these grades consist of zinc oxide, precipitated from solutions, with a large surface area, which is frequently greater than 15 m$^2$/g. A large surface area is advantageous in the present process. It is also possible to employ a zinc oxide which contains impurities which are inert under the reaction conditions for the manufacture of acetone, such as, for example, aluminum oxide or silicon dioxide. With regard to the large number of possible impurities, it is appropriate to test the particular support, under the reaction conditions, for inherent activity which reduces the selectivity.

The catalyst may be manufactured by the methods which are in themselves known for the manufacture of catalysts. Thus, for example, copper oxide, mixed with graphite and zinc oxide, can be suitably formed by tableting or extruding. It is also possible to impregnate the mixture of graphite and zinc oxide with aqueous copper salt solutions, such as copper acetate solutions or copper tetraaminecarbonate solutions, and to dry the impregnated mixture. The copper salt may then be converted into copper oxide as disclosed in U.S. Pat. No. 4,000,199 by heating in the presence of oxygen and the catalyst may then be formed in the customary manner. Suitable forms of the catalyst are balls, tablets, strands, pills or lumps. It is also possible first to manufacture molded pieces from graphite and zinc oxide, then to impregnate these, to dry the impregnated pieces and to oxidize the copper salt to copper oxide.

The copper oxide content of the catalyst is not critical. In general, a copper oxide content from about 0.1 percent by weight (relative to the ready-to-use catalyst) is sufficient for the impregnation, while a copper oxide impregnation of more than 10 percent by weight brings no added advantage, so that catalysts with a copper oxide content of 0.1 to 10 percent by weight are customarily used. Copper oxide contents between about 1 and 3 percent by weight are particularly suitable.

The reaction temperature should be kept as low as possible in order to avoid further oxidation of the acetone already formed. In general, the reaction is carried out at internal reactor temperatures of about 150° to 270° C. Although appreciable reaction also still takes place below this temperature range, the rate of reaction below 150° C. is in general too low for an industrial process. Above 270° C., the yield of acetone, relative to isobutyraldehyde employed, becomes appreciably lower. Particularly favorable results are achieved in the range from about 200° to 250° C.

The contact time which is appropriate economically is usually between about 0.1 and 10 seconds, and is preferably 0.2 to 5 seconds, calculated with the total amount of gas introduced under the reaction conditions and relative to the bulk volume of the catalyst. The contact time is thus understood as the time which the gas mixture requires, under the reaction conditions, in order to pass through the space occupied by the loose catalyst.

The reaction is usually carried out under normal pressure or under only slightly elevated pressure up to about 5 bars, but it can also be carried out under a higher excess pressure, it being necessary to observe only the conditions for maintaining the gas phase.

The two carbon oxides CO and $CO_2$ are formed as a by-product during the reaction, the proportion of CO in general being several times the $CO_2$ proportion, so that after freeing the off-gas from acetone, it can advantageously also be used as fuel gas or, after additionally removing the $CO_2$, also as a source of CO for syntheses.

Oxygen, optionally mixed with an inert diluent, is employed as the oxidizing agent. The oxygen should be employed in an amount of at least 1 mol of oxygen per mol of isobutyraldehyde, since, for stoichiometric reasons, complete isobutyraldehyde conversion cannot be achieved with lower amounts of oxygen. It is advisable to employ oxygen in molar excess relative to isobutyraldehyde, so that, even in the case of complete conversion of the isobutyraldehyde, the reaction gas still contains oxygen after passage through the catalyst bed. Air is usually employed as the oxidizing agent. It is also possible to use pure oxygen, without the addition of an inert gas. A molar excess of oxygen of more than 10%, in particular 200 to 300%, is usually employed. However, quite considerably higher excesses are also possible where pure oxygen is used.

The isobutyraldehyde content in the feed gas is appropriately 1 to 8 percent by volume. At isobutyraldehyde contents of less than 1 percent by volume, the process no longer appears economical, because of increasing separation costs for the acetone formed. In the case of isobutyraldehyde contents of over 8 percent by volume in the feed gas, the complete conversion desired can no longer be achieved economically on an industrial scale because of the high heat of reaction. The reaction is appropriately carried out within a range of from about 2 to 5 percent by volume.

Suitable inert diluents for the reactants are, in particular, nitrogen and/or steam, but the oxides of carbon contained in the off-gas of the reaction can also be used for the dilution. The use of nitrogen is favorable, since air is the cheapest and therefore the preferred oxidizing agent. The addition of steam improves the removal of the heat formed during the reaction, whereby a higher space/time yield and a better selectivity of the reaction can be achieved. Compared with non-condensable diluents, steam also facilitates the separation of acetone from the reaction gases, since the parts by volume of the non-condensable gases are correspondingly reduced. Steam is usually employed in amounts of up to 70 percent by volume, relative to the total feed gas mixture, but larger amounts of steam can also be used, which is particularly appropriate if pure oxygen is employed. Mixtures of several inert diluents can also be advantageously employed. Mixtures of air and steam, for example are very suitable. The gases issuing from the reactor can also be recycled into the reactor, after separating off the acetone formed, and used as the diluent.

Although gas mixtures which are in the explosive range can also be employed for the process according to the invention, when suitable measures are taken, non-explosive gas mixtures are nevertheless preferably employed when the reaction is carried out on a large industrial scale.

The advantages which can be achieved with the process according to the present invention are, above all, that isobutyraldehyde is converted very selectively into acetone, with high conversions, and that because of the high selectivity, only a small proportion of the isobutyraldehyde undergoes complete combustion and as a result less heat must be removed, whereby a high space/time yield is achieved.

The invention is further illustrated by the following specific examples.

EXAMPLE 1

960 g of zinc oxide are intimately mixed together with 40 g of colloidal graphite and 30 g of water and the mixture is pressed to give tablets (diameter 4 mm, thickness 4 mm) and the tablets are then dried at 110° C. for 16 hours and calcined at 350° C. for 16 hours. The finished tablets are impregnated with 122 g of a copper tetraamincarbonate solution, which contains 13.9% of copper ions, and dried at 110° C. for 16 hours and calcined at 350° C. for 16 hours. The copper II oxide content of the freshly made catalyst is 2.1 percent by weight and the graphite content is 3.9 percent by weight.

60 cm$^3$ of this catalyst are introduced into a reaction tube, thermostatically controlled with boiling water, made of standard constructional steel and having an internal diameter of 20 mm and are charged, at a reaction temperature of 220° C. and under an internal reactor pressure of 1.5 bars, with a gas mixture which consists of 3.5 percent by volume of isobutyraldehyde, 44.2 percent by volume of air and 52.3 percent by volume of steam. The gas mixture issuing from the reactor is investigated by gas chromatography. The isobutyraldehyde conversion is 99.6% and the yield of acetone, relative to the amount of isobutyraldehyde converted (selectivity), is 98 mol percent.

EXAMPLE 2

960 g of a zinc oxide support (catalyst support, type H 2004, Katalysatorenwerke Houdry-Hüls), which contains, in addition to zinc oxide, relatively small proportions of $Al_2O_3$, CaO, $K_2O$ and $Cr_2O_3$, are ground, the ground support is mixed with 40 g of colloidal graphite and 30 g of water, the mixture is pressed to give tablets with a diameter of 4 mm and a thickness of 4 mm and the tablets are dried and heated at 350° C. The support thus manufactured is impregnated with copper oxide as in Example 1. The copper II oxide content of the freshly made catalyst is 2.1 percent by weight, and the graphite content is 3.9 percent by weight. Isobutyraldehyde is then converted under the same conditions as in Example 1. The isobutyraldehyde conversion is 99% and the selectivity for acetone is 98 mol percent.

EXAMPLE 3

A catalyst with a copper II oxide content of 0.1 percent by weight and a graphite content of 4 percent by weight is manufactured analogously to Example 1. Under the reaction conditions described in Example 1, an isobutyraldehyde conversion of 95% is achieved with a selectivity for acetone of 98 mol percent.

EXAMPLE 4

A catalyst with a copper II oxide content of 6.7 percent by weight and a graphite content of 5.6 percent by weight is employed under the reaction conditions of Example 1. Conversion of isobutyraldehyde: 92%; selectivity for acetone: 97 mol percent.

EXAMPLE 5

A catalyst with a copper II oxide content of 2 percent by weight and a graphite content of 20 percent by weight is employed under the reaction conditions of Example 1. Conversion of isobutyraldehyde: 99%; selectivity for acetone: 97 mol percent.

EXAMPLE 6

Example 1 is repeated, with the exception that a gas mixture having a composition of 2.1 percent by volume of isobutyraldehyde and 97.9 percent by volume of air is employed. Conversion of isobutyraldehyde: 99%; selectivity for acetone: 96 mol percent.

EXAMPLE 7

Example 1 is repeated, with the exception that a gas mixture having a composition of 3.2 percent by volume of isobutyraldehyde, 9.7 percent by volume of pure oxygen and 87 percent by volume of steam is employed. Conversion of isobutyraldehyde: 98.6%; selectivity for acetone: 99 mol percent.

We claim:

1. In a process for the production of acetone by the catalytic, oxidative decarbonylation of isobutyraldehyde in the gaseous phase wherein a gaseous mixture of 1 to 8% by volume of isobutyraldehyde and at least a stoichiometric amount of oxygen, is contacted with a zinc oxide supported copper oxide catalyst, the improvement consisting essentially of said zinc oxide supported copper oxide catalyst having about 2.5 to 25 percent by weight graphite, based on the finished catalyst.

2. The process of claim 1, wherein said gaseous mixture is contacted with the catalyst for a time of 0.1 to 10 seconds.

3. The process of claim 2, wherein said supported catalyst has a content of said copper oxide of 0.1 to 10% by weight, based on the finished catalyst.

4. The process of claim 3, wherein said copper oxide content is 1 to 3% by weight.

5. The process of claim 4, wherein said graphite content is 3 to 10% by weight.

6. The process of claim 5, wherein said gaseous mixture contains 2 to 5% by volume of isobutyraldehyde.

7. The process of claim 2, wherein up to about 300% molar excess of oxygen is used in said gaseous mixture.

8. The process of claim 2, wherein said gaseous mixture comprises isobutyraldehyde and air.

9. The process of claim 2, wherein said gaseous mixture comprises air, isobutyraldehyde and steam.

10. The process of claim 2, wherein said oxidative decarbonylation is carried out at a temperature about 150° to 270° C.

11. The process of claim 2, wherein said oxidative decarbonylation is carried out at a temperature of about 200° to 250° C.

12. The process of claim 2, wherein said time of contact is 0.2 to 5 seconds.

13. The process of claim 1, wherein said graphite is colloidal graphite where 95% of the graphite has a particle size not more than about 4 $\mu$m.

* * * * *